United States Patent [19]
Johnson

[11] 3,992,515
[45] Nov. 16, 1976

[54] COMPOSITION FOR INDICATING AND METHOD OF REMOVING DENTAL UNDERCUTS AND THE LIKE

[76] Inventor: Vernon S. Johnson, 3642 Olympia, Houston, Tex. 77019

[22] Filed: Nov. 15, 1974

[21] Appl. No.: 524,068

[30] Foreign Application Priority Data
Dec. 5, 1973 United Kingdom............... 56310/73

[52] U.S. Cl...................................... 424/7; 106/35; 23/230 B
[51] Int. Cl.²...................... G01N 31/22; C09K 3/00
[58] Field of Search................. 106/30, 35, 239, 19, 106/285, 241; 424/7, 34; 23/230 B

[56] References Cited
UNITED STATES PATENTS

| | | | |
|---|---|---|---|
| 1,439,695 | 12/1922 | Doughty | 106/30 |
| 1,439,696 | 12/1922 | Doughty | 106/239 |
| 2,450,959 | 10/1948 | Heinecke | 106/30 |
| 3,309,274 | 3/1967 | Brilliant | 424/7 |
| 3,390,049 | 6/1968 | Rednick | 106/241 |
| 3,584,112 | 6/1971 | Morris | 106/19 |
| 3,822,343 | 7/1974 | Hill | 424/34 |

OTHER PUBLICATIONS
Chemical Dictionary — 1961, p. 751.

*Primary Examiner*—Theodore Morris
*Attorney, Agent, or Firm*—Fulbright & Jaworski

[57] ABSTRACT

A dental indicator composition useful for, among other things, indicating an undercut, binding, or restricting area on a tooth, or a laboratory model and/or procedure, the composition comprising a coloring agent, a vehicle composition for the coloring agent and a solvent. The dental indicator composition is painted on the portion of a tooth having an undercut and is removed by mechanical means thereby eliminating the undercut.

2 Claims, No Drawings

COMPOSITION FOR INDICATING AND METHOD OF REMOVING DENTAL UNDERCUTS AND THE LIKE

BACKGROUND OF THE INVENTION

In the preparation of a tooth or teeth for crowns, inlays, onlays, bridges and the like, dentists must eliminate undercuts from the tooth or teeth in question. It is undesirable to remove excessive tooth structure as would weaken the tooth or otherwise jeopardize its use as a supporting structure. With the advent of high speed drills, more tooth structure can be removed than is necessary in short order before realization of the fact.

By way of example, when a dentist prepares a patient's tooth to receive a crown or other restoration, ordinarily a high speed drill or the like is used to shape the tooth so that the non-occlusal surfaces converge toward the occlusal surface or path of insertion. If a portion of the tooth surface remains divergent, which is commonly referred to as an undercut, the metal crown will not conform to the tooth and a perfect fit cannot be obtained. Hence elimination of undercut areas is necessary.

In the case of the preparation of a tooth for an inlay, ordinarily tooth structure is removed in a manner such that the resulting inner walls diverge toward the path of insertion thereby creating a recess in which the inlay may be placed. If any portion of the recess walls are convergent instead of divergent, an undercut is created which again prevents a perfect fit of an inlay to the tooth.

Heretofore, undercuts of the nature described have been removed by visually surveying the surface of a tooth and using a drill or other suitable means to remove tooth structure as necessary. As indicated previously, a shortcoming of this procedure is that excessive tooth structure can be removed before appreciation of the fact, and it would be highly advantageous to eliminate undercuts in a more precise manner so as to avoid excessive removal of tooth structure. The present invention is directed to a composition of matter and a method of use thereof that provides such advantageous results.

SUMMARY OF THE PRESENT INVENTION

The present invention is directed to a dental indicator composition and a method of using the composition as an aid in eliminating undercuts and the like from tooth surfaces.

The composition includes a coloring agent such as a dye, a vehicle such as a gum resin for the coloring agent to effect adherence of the coloring agent to a dental surface, and a solvent for the vehicle and coloring agent. In the method of the present invention, an undercut on a tooth surface may be eliminated by painting the indicator composition on the tooth and thereafter mechanically removing substantially all of the color indicating composition from the affected area of the tooth such as by means of a drill, etc.

It is, therefore, an object of the present invention to provide a dental indicator composition for use in eliminating undercuts on a tooth.

A further object of the present invention is the provision of a dental indicator composition comprising a coloring agent, a vehicle composition for the coloring agent and a solvent.

Still a further object of the present invention is the provision of a method for eliminating undercuts on a tooth by painting a color indicating composition on the surface of the tooth, and thereafter mechanically removing substantially all of the color indicating composition from the affected area of the tooth.

Other and further objects, features and advantages will be apparent in the following description of preferred embodiments of the invention given for the purpose of disclosure.

DESCRIPTION OF THE PREFERRED EMBODIMENTS

The dental indicator composition of the present invention includes a coloring agent, a vehicle composition for the coloring agent and a solvent to solubilize both the coloring agent and vehicle therefor.

The preferred formulation of the dental indicating composition is a dye such as gentian violet as the color indicating agent although any tolerant dye or coloring agent can be used so long as the material employed exhibits visible color when applied to a dental surface.

The preferred vehicle composition for the coloring agent is a gum resin such as gum copal since it is a material exhibiting sticky or adhesive properties. In other words, the gum material absorbs and becomes vehicle for the dye and causes the dye or coloring agent to adhere to dental surfaces. While a gum resin such as gum copal is preferred, it nevertheless will be recognized that any suitable tolerant vehicle may be used so long as the material selected exhibits the necessary sticky or adhesive characteristics.

Inasmuch as most gum resins, including gum copal, are not in liquid form, a solvent must be employed to solubilize both the resin vehicle and dye or coloring agent. In the preferred embodiment wherein the dye is gentian violet and the vehicle is gum copal, the preferred solvent is a mixture of methyl alcohol, ether, and chloroform. The weight proportions of each are preferably from about 10 to about 15% methyl alcohol, from about 10 to about 15% ether, the remainder being chloroform. Ethanol may be substituted for the methyl alcohol with good results.

The amount of dye employed as a coloring agent is not critical, it being desirable to have a sufficient amount to display color upon application of the dental indicator composition to a dental surface. If gentian violet is employed, only about two drops of 2% gentian violet solution for about 30 cubic centimeters (cc) of total dental indicator composition solution will suffice.

Similarly, the amount of gum resin or gum copal employed is not critical so long as there is an amount effective to cause the dye to adhere to a dental surface.

Finally, the amount of solvent used is not critical so long as a sufficient amount is present to solubilize the dye and gum copal or gum resin.

In use, the sticky, colored indicator composition is applied to the surface of a tooth such as by means of a brush and/or cotton pellet and is allowed to dry. When the tooth is to be prepared for a crown, inlay, onlay, bridge or the like, the tooth structure is removed with a drill by conventional means. For example, the axis of the drill bit is generally parallel to, for example, the lingual or buccal surface of the tooth, or may be slightly converging toward the path of insertion in the case of a crown and diverging toward the path of insertion in the case of any inlay. As tooth structure is removed, any dye remaining indicates an undercut area which may be eliminated by further removal of tooth structure. By this technique, only the necessary amount of tooth structure is removed, a wax pattern may then be made and drawn and conventional dental procedures followed thereafter.

If a jacket preparation is being made, a shoulder is formed on the tooth at the gingvia and the dental indicator composition of the present invention is painted on the tooth with a brush or cotton pellet. The buccal tooth structure is removed with a drill as explained above and undercuts are eliminated when all the dye is removed.

Still another use of the present invention is in connection with the fitting of dental restorations that may be slightly binding. The tooth to receive the restoration or the restoration itself (or both) is painted with the dental indicator composition and the restoration is seated thereon with firm pressure. An offending restriction on the tooth surface is indicated where the dye is scraped from the tooth by the restoration. Conversely, a restriction on the restoration is indicated where the dye is scraped therefrom by the tooth. A correction may be made by eliminating the restriction preferably on the restoration. The dental indicator composition may be used in still another instance by painting the occlusal surface of the restoration therewith and, after seating the restoration, having the patient bite into centric occlusion and follow with lateral and protrusive movements. These steps will pressure-trace the dental indicator composition and indicate where to correct any imbalance of tooth movement excursion.

Advantageously, the dental indicator composition of the present invention may be removed from adjacent gingival tissue or teeth by saturating a cotton pellet with alcohol and simply wiping the color composition away. Alternatively, the composition may be removed with a Cavitron.

Thus it may be seen that the composition of the present invention is uniquely suited for use as means to detect undercut areas of a tooth structure in a manner not heretofore known or appreciated, to reveal areas that are slightly binding or restorations and bridge preparations and to reveal high spots on the occlusion of any restoration or tooth, and to relieve any binding or restricting area involving any laboratory procedure such as adjustment of clasp on removable partials, etc. Still other uses will occur to those skilled in the art.

The present invention, therefore, is well adapted to carry out the objects and attain the ends and advantages mentioned as well as others inherent therein. While a presently preferred embodiment of the invention has been given for the purpose of disclosure, numerous changes in the composition and method disclosed herein may be resorted to without departing from the spirit and scope of the invention as hereinafter claimed.

What is claimed is:
1. A dental indicator composition, comprising,
   a. a tissue tolerant dye in an amount sufficient to display color upon application of the composition to a dental surface,
   b. gum copal in an amount effective to cause the dye (a) to adhere to a dental surface, and
   c. a solvent in an amount sufficient to solubilize the dye (a) and gum copal (b) wherein the solvent includes by weight proportions from about 10% to about 15% methyl alcohol, from about 10% to about 15% ether and the remainder chloroform.
2. The dental indicator composition of claim 1 wherein the tissue tolerant dye (a) is gentian violet.

* * * * *